United States Patent [19]

Miller et al.

[11] 3,939,969
[45] Feb. 24, 1976

[54] SUTURE PACKAGE
[75] Inventors: David C. Miller, Camillus, N.Y.; Clifton C. Sutton, Somerville, N.J.
[73] Assignee: Ethicon, Inc., Somerville, N.J.
[22] Filed: July 24, 1974
[21] Appl. No.: 491,200

[52] U.S. Cl. ............... 206/63.3; 206/476; 206/484; 206/498
[51] Int. Cl.² ......................................... A61L 17/02
[58] Field of Search ........... 206/63.3, 438, 476–477, 206/482–484, 488–489, 491–492, 498; 229/85

[56] References Cited
UNITED STATES PATENTS

| | | | |
|---|---|---|---|
| 3,338,401 | 8/1967 | Regan, Jr. | 206/63.3 |
| 3,357,550 | 12/1967 | Holmes et al. | 206/63.3 |
| 3,361,253 | 1/1968 | Lonholdt | 206/438 X |
| 3,444,994 | 5/1969 | Kaepernik et al. | 206/63.3 |

FOREIGN PATENTS OR APPLICATIONS

| | | | |
|---|---|---|---|
| 705,232 | 3/1965 | Canada | 206/63.3 |
| 1,251,466 | 10/1967 | Germany | 206/63.3 |

*Primary Examiner*—William Price
*Assistant Examiner*—Steven E. Lipman
*Attorney, Agent, or Firm*—W. R. Eberhardt; A. O. Robertson

[57] ABSTRACT

An improved package for sutures in which an inner suture retainer is intimately connected to the sealed outer envelope so that when the outer envelope is opened, the suture end in the inner retainer is exposed for immediate pick-up.

9 Claims, 10 Drawing Figures

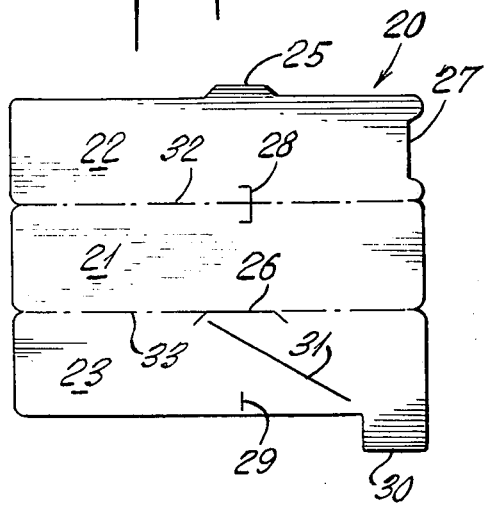
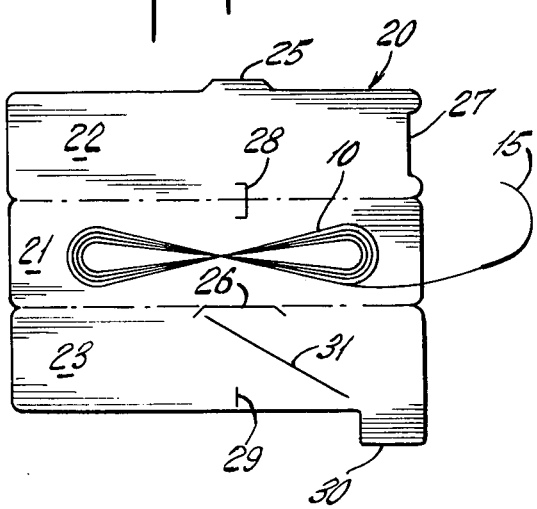
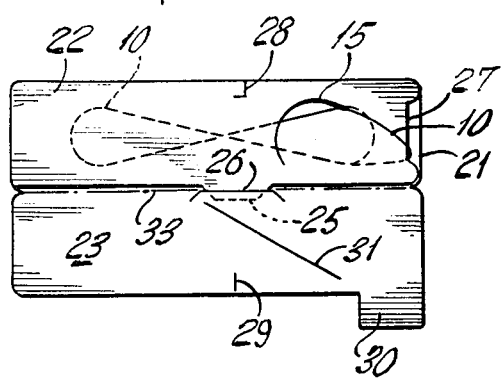
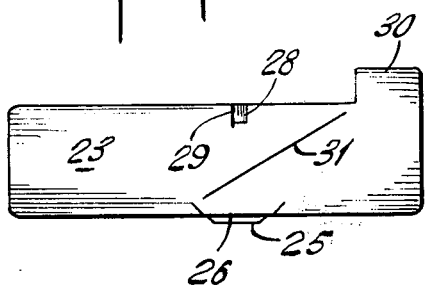
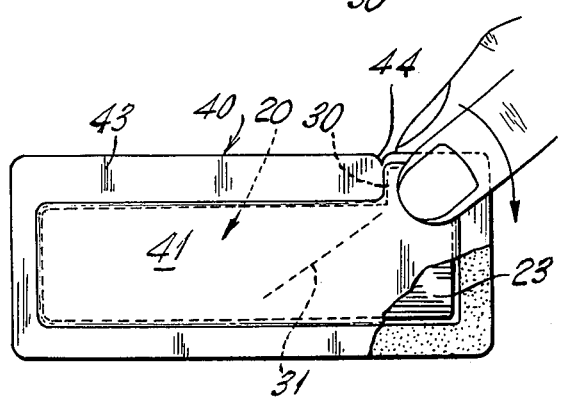
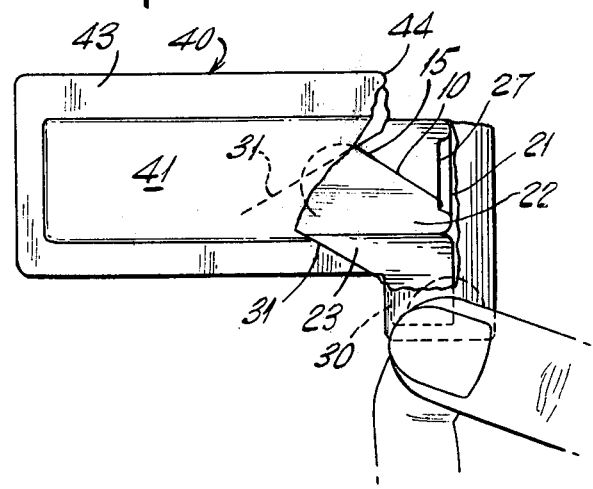

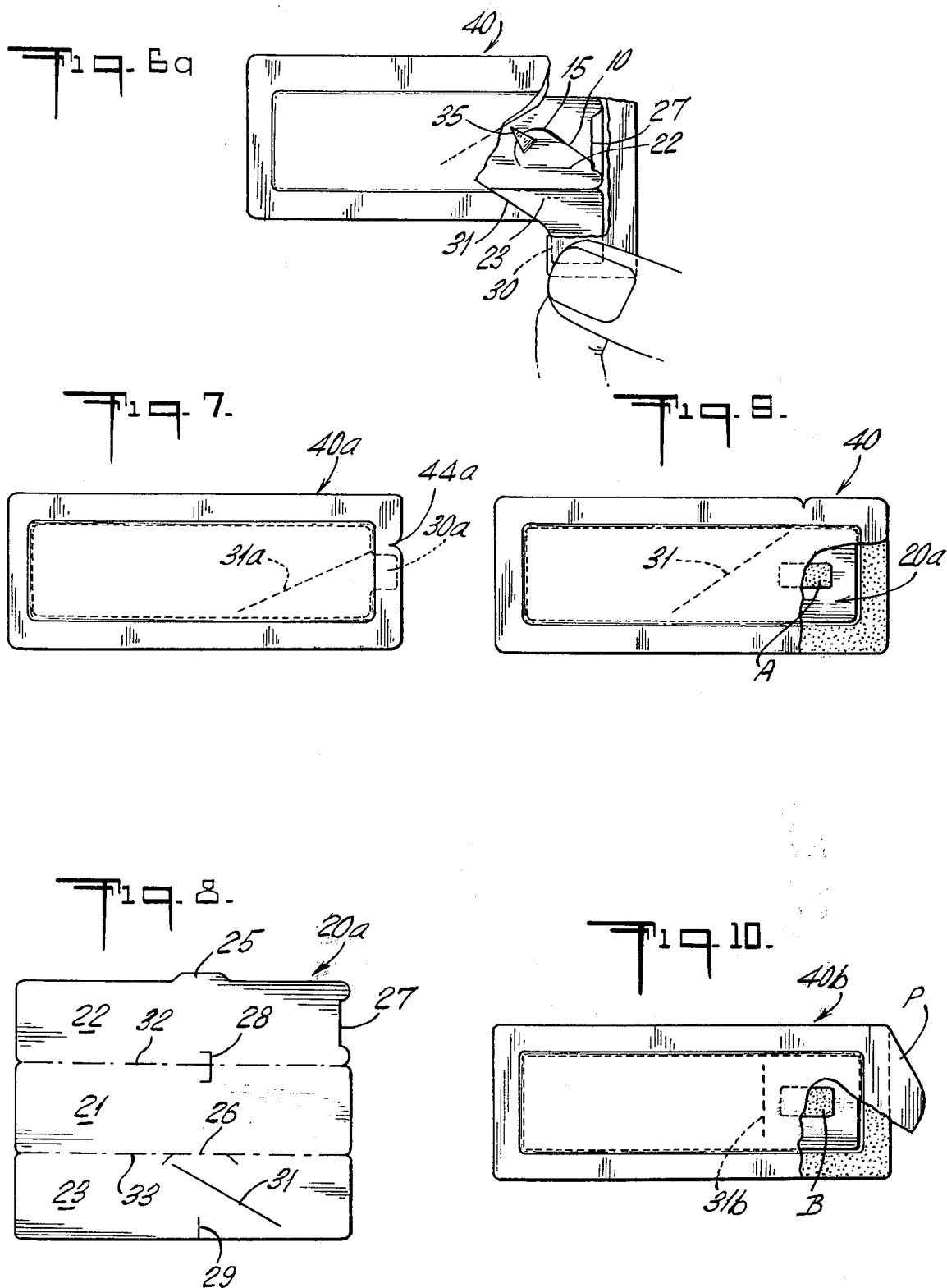

SUTURE PACKAGE

The present invention relates to packages for surgical sutures. The expression "suture" or "sutures" as herein employed refers to elongated surgical strands suitable for suturing or other surgical procedures, and includes those strands commonly called either sutures or ligatures. The expression "suture" or "sutures" also is intended to embrace sutures with needle attached as well as un-needled sutures.

A suture is normally employed in an operating room under conditions making unnecessary handling during the removal of the suture from the package undesirable. Attempts are made continually to design suture packages to minimize handling but existing packages still require several manipulative steps before the terminal portion of the suture or the needle is available for grasping. Existing packages usually comprise a hermetically-sealed envelope which first is opened by tearing or stripping to expose an inner suture retainer or a sleeve from which the suture or sutures are removed by some manipulative device. Many sutures are packaged in single suture packages in which the suture is arranged in a retainer which separates the terminal portion of the suture with or without attached needle from the bulk of the suture. Such retainers normally have multiple panels which function to separate the end of the suture and needle from the bulk of the suture and to aid in maintaining the needle in position. In suture packages with such retainers, it is necessary not only to open the package but also to remove the retainer and open the retainer before access to the needle may be had.

The present invention is directed particularly to packages containing a single suture or multiple sutures arranged in a retainer. The purpose of the present invention is to provide a suture package in such a manner that when a suture is required, it may be obtained with minimum handling in a most expeditious and efficient manner and in which the manipulative steps heretofore required are reduced or avoided. With the present invention, the steps of removing the suture retainer from the package and step of opening the retainer to expose the terminal portion of the suture are rendered unnecessary.

According to the present invention, a suture package is provided such that when the sealed envelope or packet is opened by exerting a pulling force, a portion or section of the top panel of the suture retainer simultaneously separates or detaches in such a manner as to expose the suture in a position suitable for facile and immediate pick-up. The pulling force exerted when the envelope is opened may occur both in envelopes which are opened by tearing and in envelopes which are opened by stripping. Thus, when an envelope is to be opened by tearing, the operator holds the package on both sides of the tearing notch and exerts force in opposite directions, one of which is a pulling force. When the envelope is to be opened by stripping, the operatore holds top and bottom stripping flaps and exerts a pulling force on the top flap to separate the panels or a portion thereof. The present invention is applicable to suture packages opened in either of the above ways. The invention hereinafter is described in terms of a package containing one suture but is understood to include those containing more than one suture.

The package of this invention comprises a sealed envelope of two panels sealed at the peripheral edges and a multiple-paneled inner suture retainer with the panels of the retainer preferably foldably connected to one another with the top retainer panel having a terminal detachable section and intimately connected to the sealed envelope so that a pulling force on the envelope exerts a simultaneous force on the detachable section. In the retainer, one panel functions as a support for the arranged suture, i.e., coiled, wound, etc., and there is present at least one additional panel foldably connected to the edge of the first panel and adapted to fold over the arranged suture to sandwich and secure the suture between the panels. This panel may function as the top panel with a detachable section, particularly if the suture end is held separate from the major portion of the arranged suture such as by a tab on the underside of the panel. Preferably, the retainer has at least three panels so that the panel having the primary function of securing the arranged suture is distinct from the panel having a detachable section. In a three-panel arrangement, the suture is placed on the main or first panel with the end of the suture with or without needles extending from one end of the panel which may be called the dispensing end. Thereafter, the second panel is folded over the arranged suture locking it in position and the extended suture end is folded back and placed on top of the second panel and the third panel then folded on top of the second panel locking the suture end in place. The expression "suture end" refers to the terminal portion of the suture which is to be grasped in use and is inclusive of the attached needle if the package contains a needled suture. The third panel is the top panel which is separable as hereinafter described to accomplish the objects of the present invention.

The top retainer panel is connected at one end to the envelope by a connecting device or means so that when the sealed envelope is opened by a pulling force exerted on at least a portion of the envelope, that pulling force exerts a simultaneous force on one end of the top retainer panel bringing about a separation of the top retainer panel thereby exposing the suture end. The connecting means may be a tab to be imbedded in the peripheral seal or it may be an adhesive bond as hereinafter more fully described. To aid in the separation, the top panel preferably is modified by a line of weakening extending across the panel for readily separating the top panel into two sections. A preferred line of weakening is a slit especially a single slit extending substantially across the width of the panel, but may be also several discontinuous slits or perforations. Other lines of weakness include crease, score, etc. which accomplish the same purpose. Additionally, the invention embraces a retainer in which the top panel has no line of weakening. However, inasmuch as an irregular tear of the top panel is less desirable, it is beneficial to provide a line of weakening, preferably a slit.

In one embodiment of the present invention, the top panel of the retainer is modified by the provision of a slit and a tab. The tab is the connecting means to intimately connect the inner retainer to the sealed envelope by being imbedded and sealed in the peripheral seal of the envelope at an appropriate position. Thus, when the envelope is opened by tearing or stripping, the tab is simultaneously acted upon. The tab is further related to the position of the slit so that when the tab is acted upon, a separation or detachment of a portion of the top retainer panel occurs at the position of the slit thereby exposing the needle and terminal portion of the suture.

In another embodiment of the present invention, the top panel is provided with a slit and at least that section of the panel closer to the dispensing end is secured to the envelope by an adhesive bond. The expression "adhesive bond" is intended to embrace any means which would normally impart results expressable as bonding, sealing or adhesion. Heat sealing is preferred although pressure seal or other adhesive means is suitable. The adhesive bond is applied at adjacent portions of the retainer and envelope panel and is the connecting means to connect the inner retainer to the envelope. Thus, when the envelope is opened, the section of the panel at the dispensing end remains connected to the adjacent envelope causing a separation of the panel thereby exposing the terminal portion of the suture and needle. The latter embodiment also may be used for packages opened either by tearing or stripping and is a preferred embodiment for use with packages opened by stripping.

Preferably, the present invention is employed in connection with a hermetically-sealed outer envelope which is to be opened by tearing. Such envelope is made of two panels, preferably of laminated plastic-aluminum foil with a seal extending completely around the periphery. It is usually provided with a tearing notch close to the dispensing end, i.e., the end where the suture end is located. When such envelope is opened by exerting a force in opposite directions, usually the terminal portion of the envelope is pulled frontwardly. Thus, when the connecting means is a tab, the tab is preferably positioned in the seal at the terminal portion with respect to the position of the tearing notch so that when the package is ready to be opened, the pulling motion on the terminal portion of the envelope simultaneously exerts a pulling motion on the tab and with the tearing of the outer envelope detaches a portion of the top panel exposing the suture end in a position of immediate grasping with a needle holder or other means.

When an adhesive bond is employed as connecting means, a portion of at least the terminal section of the retainer is bonded or heat sealed to the adjacent envelope panel. The terminal section of the retainer would be positioned in the packet toward the terminal portion of the packet with respect to the tearing notch. When the package is to be opened, the operative steps and the results achieved are as described above in the package in which a tab in the peripheral seal is the connecting means.

The present invention may also be employed in connection with a hermetically-sealed outer envelope which is to be opened by stripping. Such envelope also is made of two panels with a seal extending completely around the periphery, but is generally provided with stripping flaps on one end of the package which are employed to separate the panels or a portion thereof. For use with such envelope, the detachable section of the retainer is connected to the envelope at the end proximate to that provided with stripping flaps. Thus, when the stripping flaps are gripped and the top panel pulled, at least partially away, the detachable section connected to the panel separates, exposing the suture end. For use with a strippable outer envelope, an adhesive bond is preferred to intimately connect the detachable section to the envelope.

The present invention and advantages thereof will become apparent in the following detailed description and accompanying drawings which illustrate preferred embodiments contemplated by this invention but are not intended to limit the invention.

FIG. 1 is a plan view showing an unfolded suture retainer suitable for use in connection with the present invention;

FIG. 2 is a similar plan view of the retainer of FIG. 1 showing an arranged suture in the retainer, illustrated with a figure-eight coil;

FIG. 3 is a schematic plan view of the retainer and suture of FIG. 2 showing the second panel folded down over the first panel and with the curved needle and suture end positioned over the second panel;

FIG. 4 is a plan view of the retainer of FIGS. 1–3, with the panels folded together and locked into position and showing the slit and protruding tab;

FIG. 5 is a schematic plan view of a complete suture package showing the suture retainer in position and hermetically-sealed within an outer container provided with a tearing notch;

FIG. 6 is a schematic plan view showing the package of FIG. 5 after having been torn open;

FIG. 6a is a fragmentary plan view of an opened package similar to FIG. 6 showing optional use of a tab to hold the needle in position;

FIG. 7 is a schematic plan view of another embodiment showing a complete suture package with a tearing notch located at the end of the package;

FIG. 8 is a plan view of an unfolded suture retainer according to another embodiment of the invention;

FIG. 9 is a schematic plan view of a complete suture package employing a suture retainer of FIG. 8;

FIG. 10 is a schematic plan view of a complete suture package employing suture retainer similar to that of FIG. 8 in a strippable package.

Referring to the drawings, FIG. 1 shows a suture retainer 20 which comprises three panels, i.e., a first panel 21 on which the suture is to be positioned, a second panel 22 connected to one longitudinal edge of the first panel 21 along fold line 32 and a third panel 23 connected to an opposite longitudinal edge of the first panel 21 along fold line 33. The retainer may be formed from any suitable relatively stiff sheet material, such as conventional paperboard, plastic sheet such as polypropylene, heavy gauge foil, or the like. Preferably, the retainer is cut from a single sheet of material and the fold lines 32 and 33 are scored on the sheet material. The panels of the retainer are modified in the following manner. Panel 23 is provided with a tab 30 proximate to one terminal portion of the panel namely, the dispensing end, and a slit 31 extending approximately from the base of the tab across the panel 23. Although the slit is shown in the drawings to extend diagonally, it may extend vertically across the width of the panel. The slit may be substituted with any line of weakness such as a perforation, or may even be omitted entirely when the retainer is made of paperboard or other easily tearable material. Any suitable locking combinations may be employed for interlocking or securing the panels. Illustrated in FIG. 1 are (1) a locking tab 25 provided on the free longitudinal edge of panel 22 to be employed in combination with slit 26 to lock panels 21 and 22 together and (2) a foldable cut or notch 28 bridging panels 21 and 22 to be employed in combination with slit 29 on the free longitudinal edge of panel 23 to lock the retainer. In addition, panel 22 preferably is provided with notch 27 as guide for the suture end. Neither the locking combinations nor the guide notch are part of the present invention.

FIG. 2 shows suture 10 positioned on the first panel 21 of retainer 20 with the end portion of the suture including needle 15 extending beyond the end of panel 21. In FIG. 2, the suture is seen in a figure-eight coil previously described in U.S. Pat. No. 3,444,494. The suture may also be positioned on the panel in any other nonentangling manner (not illustrated). Thus, the suture may be wound on a reel and the reel positioned thereon, or the suture may be positioned in a zig-zag arrangement, or wound in a helical, spiral, circular, cross, elliptical or any other manner provided that the arrangement be such that it is untangling when it is drawn out. Other arrangement methods described or known to those skilled in the art may also be employed.

As seen in FIG. 3, the second panel 22 is folded down over the suture coil. The locking tab 25 is positioned in locking slit 26 along the fold line 33 between the first panel 21 and the third panel 23.

FIG. 3 illustrates how the suture 10 including needle 15 which is shown extending beyond the dispensing end of panel 21 in FIG. 2 is curved back and superimposed over the second panel 22. Curved notch 27 on the dispensing end of the second panel 22 is useful in guiding the suture into an appropriate position but is not necessary nor part of the present invention. When the suture is wound in some other configuration, e.g., zig-zag, elliptical, coil, reel, etc., it is also curved back and superimposed on the second panel 22. Panel 22 may be provided with notch 27 or equivalent as a guide for the suture in any of the winding configurations.

After the end of the suture 10 including needle 15 have been positioned over the second panel 22, roughly as shown in FIG. 3, the third panel 23, is folded over the suture end thereby locking the second panel 22 in position and retaining the suture end firmly between the second and third panels. For this purpose, a locking combination is provided at the free longitudinal edge of the third panel 23 and along the folded longitudinal edge between panels 22 and 21. The illustrated locking combination is a cut 28 and slit 29 combination, cut 28 being seen in FIGS. 1 and 2 in an unfolded form. FIG. 4 shows cut 28 inserted in slit 29 locking the panels together.

Although the foregoing locking device is convenient, other locking means may be employed; locking means do not constitute part of the present invention. Thus, for example, another locking combination (not illustrated) would be a rectangular notch centered on the fold line between the first and second panels to be employed with a locking tab on the outer longitudinal edge of the third panel cut with inclined edges so that the edges are wider than the notch at the ends. The locking combinations to be employed lock the third panel securely to the first and second panels.

FIG. 4 illustrates the retainer in a folded and locked position showing the tab 30 which is to be placed in the seal of the outer envelope. The slit 31 which extends across the panel starts substantially at the base of the tab. A very small section of the panel preferably is left uncut before the start of the slit. The portion left uncut should be sufficiently small so that a separation of the terminal portion of panel 23 will readily occur when there is a pull exerted on the tab while holding the remainder of the retainer in position. The angle of the slit is not critical. although a diagonal slit is preferred, the slit may extend straight across the width of the panel. Moreover, in the case of sutures with needle attached, it is desirable to position the slit in a manner such that when the package is opened, the needle while visible and accessible is held in place by the undetached portion of the top panel.

FIGS. 5 and 6 illustrate the complete suture package before and after opening according to one embodiment of the present invention.

FIG. 5 illustrates folded retainer 20 containing a suture packaged in a hermetically-sealed envelope 40, of the type adapted to be opened by tearing. The envelope has front panel 41 and back panel (not shown) joined by a peripheral seal 43, and a tearing notch 44 along one longitudinal edge proximate to one end of the envelope which serves as the dispensing end. When the retainer 20 is packaged in the envelope 40, the tab 30 of the retainer is sealed into the peripheral seal 43. The retainer is placed in the envelope 40 in such a manner that the tab 30 is positioned in the seal in a direction which is toward the end of the envelope with respect to the tearing notch. The tab 30 provides a communication between the outer envelope and inner retainer and is designed to cooperate with the tearing notch 44 so that when the package is opened by tearing the end portion frontwardly and downwardly (see also FIG. 6), the tab 30 is simultaneously pulled frontwardly and downwardly causing the top panel 23 of the retainer to separate along the slit 31 thereby partially exposing the end of the suture 10 including needle 15 lying below the top panel.

FIG. 6 illustrates the tear-open package after it has been opened. The front panel 41 of the outer envelope has been pulled frontwardly starting at the tearing notch 44 with a major portion of the top panel 23 still in position in the package and the end portion of panel 23 connected to the tab 30 having been pulled forward and separated at the slit 31. A portion of second panel 22 is seen as having been exposed by the separation of a portion of panel 23; on top of panel 22 is seen the needle 15 and the end portion of suture 10 which is seen to emerge to notch 27 from between panel 22 and panel 21, the latter being visible only where panel 22 is cut away at notch 27. The needle is seen to be held in place by the undetached portion of panel 23. It can readily be seen from FIG. 6 that after a single motion of opening the package the suture end or needle is exposed ready to be grasped for its intended use.

It is noted in FIG. 6 that the needle is held in position by the undetached portion of the top panel 23. In the case of packages of finer sutures and smaller suture needles, a diecut tab, a slit or even a hole optionally may be incorporated on panel 22 to assist in positioning and/or retaining the needle or in immobilizing the needle for more ready grasping. FIG. 6a illustrates a package similar to that of FIG. 6 after opening showing needle 15 being held in place with a diecut tab 35 on panel 22.

Although the positioning of the tearing notch along one longitudinal edge with the tab imbedded in the seal toward the end of the envelope as a connecting means constitutes a preferred embodiment, the tearing notch may be positioned at the terminal edge of the envelope. When the tearing notch is at the terminal edge, a modified retainer is employed. Such retainer would have the tab along the terminal edge and the slit would form a shallower diagonal. The tab would then be imbedded in the seal at the end of the envelope.

FIG. 7 illustrates the tear-open type envelope 40a with a tearing notch 44a and a tab 30a imbedded in the seal at the end.

The invention has been described and illustrated in detail above in terms of a preferred embodiment of the present invention namely one in which a tab imbedded in the peripheral seal is the connecting means connecting the detachable section of the retainer to the envelope.

The invention also embraces the use of adhesive bond such as heat seal, pressure seal, other adhesive means, etc. for connecting the detachable section of the retainer to the envelope. In this modification, the detachable section of the retainer and adjacent envelope panel are bonded by an adhesive bond so that when the envelope is opened, the detachable portion of the top panel of the retainer simultaneously separates exposing the suture end.

FIGS. 8–9 illustrate a modified package construction which differs from the embodiment of FIGS. 1–7 in that the detachable section of the retainer is connected to the envelope by bonding. FIG. 8 is a plan view showing an unfolded suture retainer 20a according to another preferred embodiment of the present invention. It is substantially identical to the retainer shown in FIG. 1 except that it is lacking in the tab 30 of FIG. 1. The suture may be positioned in any desirable manner on panel 21 and the panels folded and the suture locked in place in a manner similar to that illustrated in FIGS. 3–4.

FIG. 9 is a schematic plan view with parts broken showing the complete suture package of a hermetically-sealed envelope 40 with suture retainer 20a in position and showing preferred area of bonding or adhesion A of the retainer to the envelope.

The procedure for opening the package is the same as seen in FIGS. 5–6. Thus, when the envelope is opened by pulling forward the terminal portion with respect to the tearing notch, the detachable portion of the retainer is simultaneously pulled away exposing the suture end including the needle.

FIG. 10 illustrates still another embodiment of the invention, namely, one in which the invention is employed with an envelope which is of a pull-open or strip-open type. FIG. 10 shows folded retainer 20a packaged in a hermetically-sealed envelope 40b with the detachable section of the retainer intimately connected to the envelope by bonding at B. When the envelope is opened by pulling away on the top stripping panel at pull tab P, the detachable section of the retainer pulls away at slit 31b exposing the suture end. In a package employing this opening method, the slit 31b on the top panel defining the detachable section is preferably placed across the panel at right angles to the length rather than diagonally across the panel.

In addition to the foregoing, a pull-open or strippable package may employ a tab as connecting means, but is less preferred.

In describing the foregoing embodiments of the present invention, the suture retainer shown has been a three-panel suture retainer and the suture was coiled in a figure-eight coil. However, sutures wound or positioned in other ways which permit drawing out without tangling may be employed. Although a three-panel arrangement for retainer is preferred since it permits separation of the needle and suture from the remainder of the suture by inclusion of a panel for this purpose, a two-panel arrangement may be employed with the second panel as the partially detachable panel. Alternatively, a four-panel arrangement is also feasible provided the panel arrangement is such that all the panels be open at the end from the suture is to be drawn, i.e., the dispensing end and provided that the needle is positioned immediately below the top partially detachable panel.

The package of this invention is useful in connection with the packaging of both relatively stiff sutures such as monofilaments and relatively flexible sutures such as braids. These materials may be natural or synthetic in origin and be absorbable or non-absorbable. Some specific suture materials applicable in connection with this invention are braided and twisted silk, braided and monofilament nylon, coated and uncoated polyester, catgut, braided and monofilament polypropylene and polyethylene, cotton, linen, homopolymers and copolymers of glycolide and lactide. This invention is, however, not limited to these materials which are listed for illustrative purposes.

The package is further adapted to be employed using any of the conventional methods of sterilization such as for example radiation, ethylene oxide, steam, etc.

Having described in the invention in specific detail and exemplified the manner in which it may be carried into practice, it will be apparent to those skilled in the art that innumerable variations, applications, modifications and extensions of the basic principles involved may be made without departing from its spirit or scope. It is to be understood that the foregoing is merely exemplary and the present invention is not to be limited to the specific form or arrangement of parts herein described and shown.

What is claimed is:

1. A suture package comprising (a) a sealed envelope and (b) an inner suture retainer intimately connected to said envelope and containing at least one suture, said sealed envelope comprising two panels sealed at the peripheral edges and adapted to be opened by a pulling force exerted on at least a portion of the envelope, said inner retainer comprising multiple panels, foldably connected to one another and folded together with the suture positioned and retained between said panels;

wherein the top retainer panel of said retainer has a terminal detachable section intimately connected to the envelope at a place near the end where a pulling force is to be exerted so that when the sealed envelope is opened by the pulling force, the pulling force exerts a simultaneous force on the top retainer panel bringing about a separation of said detachable section of said panel thereby exposing the suture end.

2. A suture package according to claim 1, wherein the envelope is provided with a tearing notch and is adapted to be opened by pulling the terminal portion of the package.

3. A suture package according to claim 1, wherein the envelope is provided with stripping flaps and is adapted to be opened by pulling the top stripping flap.

4. A suture package comprising: (a) a sealed envelope and (b) an inner suture retainer intimately connected to said envelope and containing at least one suture, said sealed envelope comprising two panels sealed at the peripheral edges and adapted to be opened by a pulling force exerted on at least a portion of the envelope; said inner retainer comprising multiple panels, foldably connected to one another and folded together with the suture positioned and retained between said panels; wherein the top panel of said retainer has a detachable section defined by a line of weakening extending approximately across the width of the panel;

and wherein said detachable section is intimately connected to the envelope by a connecting means so that when the sealed envelope is opened by a pulling force exerted on at least a portion of the envelope, the pulling force on the envelope exerts a simultaneous force on the detachable section of the top retainer panel bringing about a separation of said section along the line of weakening thereby exposing the suture end.

5. A suture package according to claim 4, wherein the connecting means connecting the detachable section of the top panel of the suture retainer to the envelope is a tab intimately imbedded and sealed in the peripheral seal of the envelope.

6. A suture package according to claim 4, wherein the connecting means connecting the detachable section of the top panel of the suture retainer to the envelope is an adhesive bond bonding adjacent portions of the retainer and envelope.

7. A suture package according to claim 4, wherein the line of weakening is a slit.

8. A suture package for needled sutures comprising: a sealed envelope and an inner suture retainer intimately connected to said envelope and containing at least one suture with needle attached, said sealed envelope comprising two panels sealed at the peripheral edges and adapted to be opened by a pulling force exerted on at least a portion of the envelope; said inner retainer comprising multiple panels, foldably connected to one another and folded together with the suture positioned and retained between said panels, wherein the top panel of said retainer has a detachable section defined by a slit extending approximately across the width of the panel;

and wherein said detachable section is intimately connected to the envelope by a connecting means so that when the sealed envelope is opened by a pulling force exerted on at least a portion of the envelope, the pulling force on the envelope exerts a simultaneous force on the detachable section of the top retainer panel bringing about a separation of said section along the slit thereby exposing the terminal portion of the suture and the needle.

9. A suture package comprising (a) a peripherally sealed outer envelope provided with a tearing notch near one end of the envelope, and (b) an inner suture retainer comprising multiple panels foldably connected to one another along its longitudinal edge and adapted to retain an arranged suture therein wherein the top panel of said retainer is provided with a tab and a slit extending approximately across the width of the panel;

wherein said tab is imbedded and sealed in the peripheral seal of the envelope adjacent to the tearing notch in the direction of the terminal portion of the envelope and the slit starts near the base of the tab at a longitudinal position substantially corresponding to the position of the tearing notch.

* * * * *